United States Patent
Rajagopalan et al.

(10) Patent No.: US 8,060,193 B2
(45) Date of Patent: *Nov. 15, 2011

(54) SYSTEMS AND METHODS FOR GRAPHIC DISPLAY OF ST-SEGMENT DEVIATION

(75) Inventors: Cadathur Rajagopalan, Dumont, NJ (US); Scott Eaton, Briarcliff Manor, NY (US); Joe Petruzzelli, Paramus, NJ (US); Jack Balji, Mahwah, NJ (US)

(73) Assignee: Mindray DS USA, Inc., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/044,306

(22) Filed: Mar. 9, 2011

(65) Prior Publication Data

US 2011/0160606 A1 Jun. 30, 2011

Related U.S. Application Data

(63) Continuation of application No. 12/372,580, filed on Feb. 17, 2009, now Pat. No. 7,925,337.

(51) Int. Cl.
*A61B 5/04* (2006.01)
(52) U.S. Cl. ........................................ 600/523
(58) Field of Classification Search .................. 128/898; 600/515, 517, 523; 604/500; 607/4
See application file for complete search history.

(56) References Cited

U.S. PATENT DOCUMENTS 7,725,171 B1 * 5/2010 Zhu et al. ...................... 600/509
2005/0191278 A1 * 9/2005 Pressler et al. ............... 424/93.2
* cited by examiner

*Primary Examiner* — George Manuel
*Assistant Examiner* — Robert Wieland
(74) *Attorney, Agent, or Firm* — Kory D. Christensen; Stoel Rives LLP

(57) ABSTRACT

Systems and methods are provided for monitoring a patient and graphically representing ST-segment deviations. A receiver acquires, from a plurality of leads, electrocardiogram (ECG) signals that each includes an ST-segment. A processor processes the ECG signals to determine baseline and current ST-segment deviations relative to an isoelectric value. A display module displays a graph that includes a first axis representing ST-segment deviation values and a second axis representing the plurality of leads. At each location along the second axis representing a respective lead, the graph displays a first set of graphic indicia representing the baseline ST-segment deviations and a second set of graphic indicia representing the current ST-segment deviations. In certain embodiments, the graphic indicia are represented by bar graphs. In other embodiments, the graphic indicia are represented by symbols that may be connected by line segments.

16 Claims, 10 Drawing Sheets

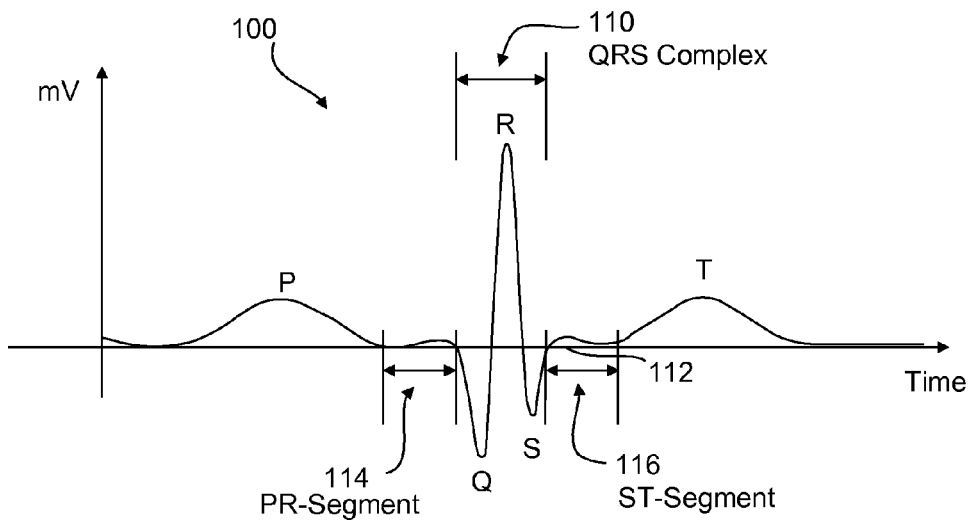
FIG. 1
(Prior Art)
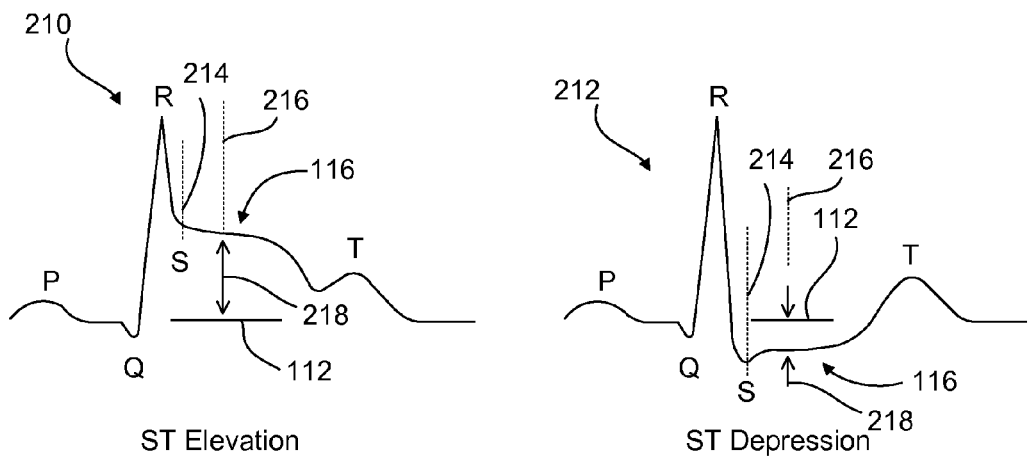
FIG. 2A
(Prior Art)
FIG. 2B
(Prior Art)

```
300 ─┐
     ┌─────────────────────────────────────┐
     │ S   I    1.4    aVL 0.4   V3  2.4   │
     │ T   II   2.0    aVF 1.3   V4  2.7   │
     │(mm) III  0.6    V1  0.6   V5  2.4   │
     │     aVR -1.7    V2  1.3   V6  1.7   │
     └─────────────────────────────────────┘
```

```
300 ─┐
     ┌─────────────────────────────────────┐
     │ S   I    1.4 (0.6)    V1 0.6 (0.3)  │
     │ T   II   2.0 (0.9)    V2 1.3 (0.7)  │
     │(mm) III  0.6 (0.3)    V3 1.0 (1.2)  │
     │                                     │
     │     aVR -1.7 (-0.8)   V4 0.5 (1.2)  │
     │     aVL 0.4 (0.2)     V5 2.4 (1.1)  │
     │     aVF 1.3 (0.6)     V6 1.7 (0.7)  │
     └─────────────────────────────────────┘
```

SYSTEMS AND METHODS FOR GRAPHIC DISPLAY OF ST-SEGMENT DEVIATION

CROSS-REFERENCE TO RELATED APPLICATION(S)

This application is a continuation of U.S. patent application Ser. No. 12/372,580, filed Feb. 17, 2009, now U.S. Pat. No. 7,925,337, which is incorporated herein by reference in its entirety.

TECHNICAL FIELD

This disclosure generally relates to cardiac analysis.

SUMMARY

Systems and methods are provided for graphically representing the progression of ST-segment deviation in one or more electrocardiogram (ECG) signals.

In one embodiment, a receiver acquires, from a plurality of leads, electrocardiogram (ECG) signals that each includes an ST-segment. A processor processes the ECG signals to determine baseline and current ST-segment deviations relative to an isoelectric value. A display module displays a graph that includes a first axis representing ST-segment deviation values and a second axis representing the plurality of leads. At each location along the second axis representing a respective lead, the graph displays a first set of graphic indicia representing the baseline ST-segment deviations and a second set of graphic indicia representing the current ST-segment deviations. In certain embodiments, the graphic indicia are represented by bar graphs. In other embodiments, the graphic indicia are represented by symbols that may be connected by line segments.

Additional aspects and advantages will be apparent from the following detailed description of preferred embodiments, which proceeds with reference to the accompanying drawings.

BRIEF DESCRIPTION OF THE DRAWINGS

FIG. 1 graphically represents a typical ECG signal of a normal, healthy person that includes a P wave, a Q wave, an R wave, an S wave, and a T wave;

FIGS. 2A and 2B graphically represent respective ECG signals that differ from the typical ECG signal shown in FIG. 1;

DETAILED DESCRIPTION

Figures 3A, 3B, 4:
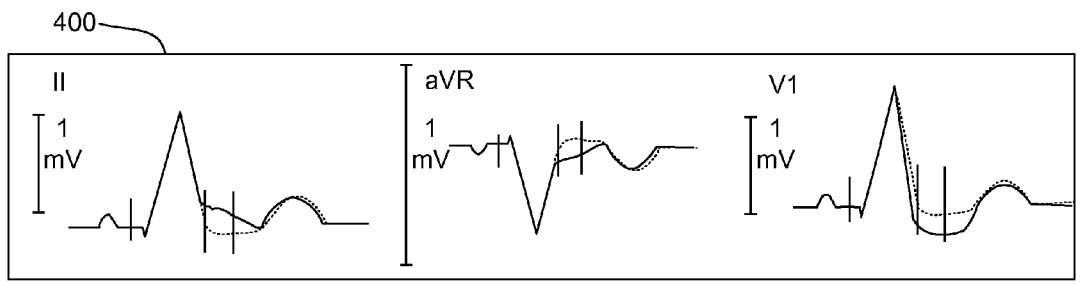
FIGS. 3A and 3B graphically represent typical user interfaces that numerically display ST-segment deviation values for a plurality of leads.
FIG. 4 graphically illustrates a typical user interface of a patient monitor displaying baseline and current ECG signals from three different leads.

Electrical waves cause the heart muscle to pump. These waves pass through the body and may be measured using electrodes attached to a patient's skin. Electrodes on different sides of the heart measure the activity of different parts of the heart muscle. An electrocardiogram (ECG) displays voltages between pairs of electrodes (leads) from different directions. Thus, an ECG may be used to display an overall rhythm of the heart and weaknesses in different parts of the heart muscle.

ECGs are used to measure and diagnose abnormal rhythms of the heart, including abnormal rhythms caused by damage to the conductive tissue that carries electrical signals. The ECG may be measured using various lead systems. Generally, the ECG is obtained by using a standard 12-lead arrangement, but it can be obtained by using other lead systems including, for example, a 5-lead system or a 3-lead system.

When patients have myocardial ischemia or injury, an ST portion (discussed below) of the ECG signal in affected leads may deviate from an isoelectric line. The affected leads may indicate an ST elevation from the isoelectric line, and the reciprocal leads may indicate ST depression from the isoelectric line. Cardiologists quantify ST-segment deviation in the affected leads to identify which patients with ST elevation myocardial infarctions (STEMI) are at greater risk and may need more aggressive intervention.

Patient monitors typically display ST-segment deviation values in millimeters where 100 μV=1 mm. Looking at a set of numerical values, however, may not be the easiest or quickest way to integrate the information from multiple leads and determine whether an ischemic state is getting worse or improving. Thus, according to certain embodiments disclosed herein, ST-segment deviations corresponding to monitored leads are graphically displayed so that a user (e.g., a clinician) can get a more complete picture of changes in a patient's condition over time. Because limb leads and precordial leads represent different planes, ST-segment deviations for the two sets of vectors are presented in some embodiments on two separate graphs.

In certain embodiments disclosed herein, systems and methods are provided for monitoring and graphically displaying ST-segment deviations to a user in a way that allows for quick and simple evaluation of trends in the patient's condition. Bar graphs, plots, or line graphs may be used to illustrate baseline and current ST-segment deviation values. Highlighting may also be used to distinguish between the baseline and current ST-segment deviation values and/or to emphasize changes in the difference between the baseline and current ST-segment deviation values.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions.

FIG. 1 graphically represents one beat of a typical ECG signal 100 of a normal, healthy person that includes a P wave, a Q wave, an R wave, an S wave, and a T wave. The P wave indicates atrial depolarization. The initial portion of the P wave is largely a reflection of right atrial depolarization and the terminal portion is largely a reflection of left atrial depolarization. When visible, the Q wave is any initial downward deflection after the P wave. The typical Q wave represents septal depolarization. The R wave is the first upward deflection after the P wave and represents early ventricular depolarization. The S wave is the first negative deflection after the R wave and represents late ventricular depolarization. The T wave is normally upright, somewhat rounded and slightly asymmetric. The T wave represents repolarization of the ventricles. A QRS complex 110 begins at the onset of the Q wave and ends at the endpoint of the S wave. The QRS complex 110 represents the duration of ventricular depolarization.

Generally, little or no electrical activity is visible along an isoelectric line 112 during a PR-segment 114 and an ST-segment 116 of the ECG signal 100. The PR-segment 114 begins at an endpoint of the P wave and ends at the onset of the QRS complex 110. During the PR-segment 114, an electrical impulse travels from the AV node through the conducting tissue (bundle branches and Purkinje fibers) towards the ventricles. Thus, the PR-segment 114 corresponds to the time it takes for the electrical impulse to reach the ventricles from the AV node. Most of the delay in the PR-segment 114 occurs in the AV node. The ST-segment 116 begins at the endpoint of the S wave and ends at the onset of the T wave. During the ST-segment 116, the atrial cells are relaxed and the ventricles are contracted so that electrical activity may not be visible. In other words, as indicated above, the ST-segment 116 is normally isoelectric.

FIGS. 2A and 2B graphically represent one beat of respective ECG signals 210, 212 that differ from the "typical" ECG signal 100. As shown in FIGS. 2A and 2B, the ST-segment 116 may experience elevation (FIG. 2A) or depression (FIG. 2B) from the isoelectric line 112 in a vertical direction. ST-segment elevation or depression may occur, for example, with cardiac injury, ventricular aneurysms, Prinzmetals angina, pericarditis, myocardial ischemia, or other diseases. An artisan will recognize from the disclosure herein that ST elevation shown in FIG. 2A and the ST depression shown in FIG. 2B may occur in the same patient as detected through different leads.

FIGS. 2A and 2B also illustrate locations of respective J-points 214 and ST-points 216. The J-point 214 is a junction between the QRS complex 110 and the ST-segment 116. The ST-point 216 is a selected time duration from the J-point 214 and the amplitude of the ST-segment is measured at this point. For example, traditional ST-segment measurements may be made at approximately $\frac{1}{16} \times$R-R interval post J-point, where the R-R interval is the heart beat interval or distance between a selected point on one ECG beat to the corresponding point on the succeeding beat. This corresponds, for example, to a 60 msec post J-point time at a heart rate of approximately 60 beats per minute. Generally, the ST-point 216 is selected to be between approximately 40 msec and approximately 80 msec after the J-point.

As shown in FIGS. 2A and 2B, the ST-segment deviation 218 is the vertical distance between the isoelectric line 112 and the ST-point 216. The voltage (vertical distance) between the isoelectric line 112 and the ST-point 216 is typically measured in microvolts. Generally, however, ECG signals are often recorded on a strip chart recorder (not shown) with a scale of 1 cm/mV and ST-segments are conventionally read in millimeters where 1 mm is equivalent to 0.1 mV.

ST-segment deviation values in millimeters are typically displayed on either an ECG section (tile) or on a separate ST parameter tile on a patient monitor. For example, FIG. 3A graphically represents a user interface 300 of a patient monitor (not shown) that displays ST-segment deviation values (in millimeters) for a plurality of leads. Looking at the user interface 300 of numerical values, however, is not the easiest or quickest way to integrate the information from multiple leads (e.g., leads I, II, III, aVR, aVL, aVF, V1, V2, V3, V4, V5, and V6) to determine whether or not ischemia is present and where such ischemia may be located.

As shown in FIG. 3A, such a display may be very cluttered, which makes it difficult to quickly glean important or relevant information from the user interface 300. Further, the typical user interface 300 of numeric information corresponding to current ST-segment deviation values provides no information to help a user determine whether the ischemia is improving or getting worse because it does not display any initial or baseline ST-segment deviation values. As shown in FIG. 3B, providing such information would make the user interface 300 shown in FIG. 3 even more cluttered because it would display 24 numerical values instead of 12 numerical values. In FIG. 3B, the user interface 300 displays the initial ST-segment deviation (shown in parenthesis) as well as the current ST-segment deviation.

ST-segment deviation may also be illustrated by overlaying a baseline ECG signal with a current ECG signal. For example, FIG. 4 graphically illustrates a user interface 400 of a patient monitor (not shown) displaying baseline and current ECG signals from three different leads (e.g., leads II, aVR, and V1). In the example shown in FIG. 4, the baseline ECG signals are shown in dashed lines and the current ECG signals are shown in solid lines. A user may manually determine the ST-segment deviations of the three leads by comparing the baseline ECG signals with the current ECG signals, or the ECG signals may be automatically calculated and displayed in a separate tile, such as the user interface 300 shown in FIG. 3. A disadvantage of overlapping baseline and current ECG signals, as shown in FIG. 4, is that such displays are typically small and cluttered. Thus, such displays typically include ECG waveforms from only a few leads, are not combined with numerical data, and provide little or no trend information (e.g., they do not indicate whether the ST-segment deviation is currently increasing or decreasing.

Thus, the embodiments disclosed herein graphically represent ST-segment deviation to allow a user to quickly evaluate a patient's current condition as well as trends in the patient's condition. A graphical method according to one embodiment displays both the initially learned values (e.g., baseline values) and current ST-segment deviation values for all, or a selected subset, of the leads. In certain embodiments, different colors are used to indicate the baseline values and the current values. In addition, or in other embodiments, information corresponding to limb leads is displayed in a first window and information corresponding to precordial leads is displayed in a second window.

Figure 5A:
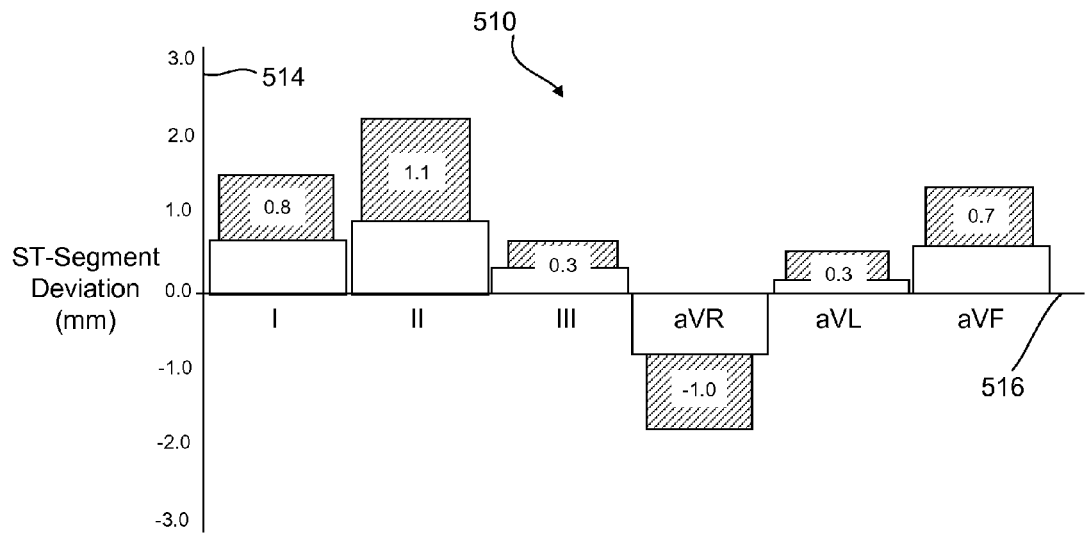
FIGS. 5A and 5B graphically illustrate respective user interfaces displaying bar graphs to represent ST-segment deviations for a selected plurality of leads according to certain embodiments.
Figure 5B:
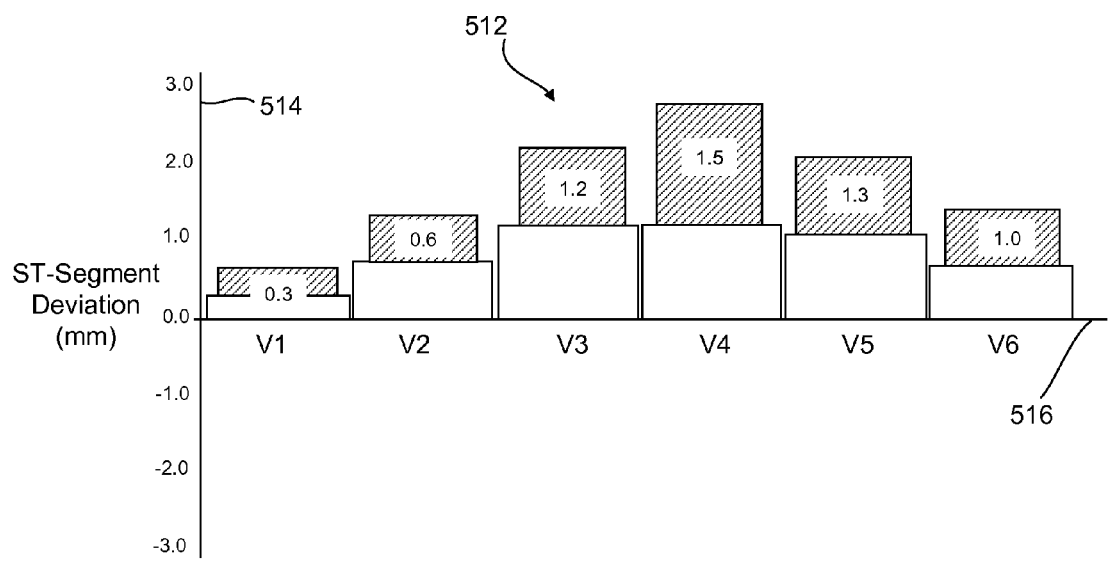

FIGS. 5A and 5B graphically illustrate respective user interfaces 510, 512 displaying bar graphs to represent ST-segment deviations for a selected plurality of leads according to certain embodiments. As discussed below, using a series of bar graphs allows ST-segment deviation data for multiple leads to be displayed together, while providing that data for each lead is represented as a separate graphical object. Each user interface 510, 512 may be displayed, for example, in a different window or portion of a patient monitor. Each user interface 510, 512 includes a first linear axis 514 representing ST-segment deviation values (in millimeters) and a second linear axis 516 representing the respective plurality of leads. In this example, the second linear axis 516 intersects the first linear axis 514 at 0.0 mm. Thus, the second linear axis 516 is displayed so as to correspond to the isoelectric value.

In the example embodiment shown in FIG. 5A, the user interface 510 displays the names of limb leads (e.g., I, II, III, aVR, aVL, and aVF) at respective locations along the second linear axis 516. In the example embodiment shown in FIG. 5B, the user interface 512 displays the names of precordial leads (e.g., V1, V2, V3, V4, V5, and V6) at respective locations along the second linear axis 516. In certain embodiments, a user may select how many and which particular leads are displayed along the second linear axis 516. In addition, or in other embodiments, the user may selectively combine limb leads and precordial leads on the same axis 516.

At each respective lead location along the second linear axis 516, a first bar graph (illustrated without highlighting) represents a baseline ST-segment deviation for the corresponding lead. The respective baseline ST-segment deviation values may be acquired, for example, when the leads are initially attached to the patient, after treatment is provided to the patient (e.g., upon administering a thrombolytic), or at any user-selected time. Because ST-segment deviation is measured relative to the isoelectric line, each of the first bar graphs extends from the second linear axis 516 (at 0.0 mm) to its respective baseline ST-segment deviation value, which is indicated along the first linear axis 514.

Further, at each respective lead location along the second linear axis 516, a second bar graph (illustrated with highlighting) represents a current ST-segment deviation for the corresponding lead. The respective current ST-segment deviation values may be updated periodically as additional data is acquired through the leads attached to the patient. Generally, users may be interested in the difference between the baseline and current ST-segment deviations. Thus, as shown in FIGS. 5A and 5B, each of the second bar graphs begins at its respective baseline value (e.g., the end of the first bar graph for the corresponding lead) and ends at its current ST-segment deviation value, as indicated along the first linear axis 514. Thus, the difference between baseline and current ST-segment deviations for a plurality of leads may be quickly and easily evaluated by the user.

As shown in FIGS. 5A and 5B, in certain embodiments, the second bar graph at each location along the second linear axis 516 may be highlighted to clearly indicate the difference between the baseline and current ST-segment deviations. In other words, the height of each of the highlighted bars represents a relative change in ST-segment deviation for the respective lead. Thus, for example, by observing changes in the highlighted areas of the user interfaces 510, 512, the user can quickly gauge whether ST-segment deviation is increasing or decreasing without translating a series of numbers.

For illustrative purposes, the examples provided herein show the highlighting as hatching (e.g., a series of slanted parallel lines). However, an artisan will recognize from the disclosure herein that any type of highlighting may be used such as shading, coloring, or the use of other graphical elements. Further, an artisan will recognize from the disclosure herein that two or more of the second bar graphs may have different highlights. For example, the second bar graph illustrating the current ST-segment deviation for the lead aVR may be a first color and the second bar graph illustrating the current ST-segment deviation for the lead aVL may be a second color. In addition, or in other embodiments, the first bar graph at each location along the second linear axis 516 may also be highlighted. For example, the first bar graph illustrating the baseline ST-segment deviation for the lead V2 may be a first color and the second bar graph illustrating the current ST-segment deviation for the lead V2 may be a second color.

In certain embodiments, the user interfaces 510, 512 also display numerical values associated with the first bar graphs, the second bar graphs, and/or the difference between the respective first bar graphs and the second bar graphs. In the embodiments shown in FIGS. 5A and 5B, the difference between each lead's baseline ST-segment deviation value and current ST-segment deviation value is displayed. For example, the numerical value "0.8" is displayed in the second bar graph corresponding to the lead I. As shown in FIG. 5A, because the baseline ST-segment deviation value is 0.6 mm and the current ST-segment deviation value is 1.4 mm, the displayed text "0.8" is an indication of the difference between the baseline and the current values for the lead I. An artisan will recognize from the disclosure herein that the display of the numerical values is not limited to a location within the area of the second bar graph. For example, such numerical values may be displayed within the area of the first bar graph, at the boundary between the first bar graph and the second bar graph, or proximate the area of the first bar graph or the second bar graph.

As shown in FIGS. 5A and 5B, in certain embodiments, the width (in the direction of the second linear axis) of the second bar graph is narrower than the width of the first bar graph corresponding to the same lead. This further helps to clearly separate the current ST-segment deviation from the baseline ST-segment deviation for a particular lead. This is also useful, for example, when an ST-segment deviation value changes direction as compared to its baseline value.

Figure 6:
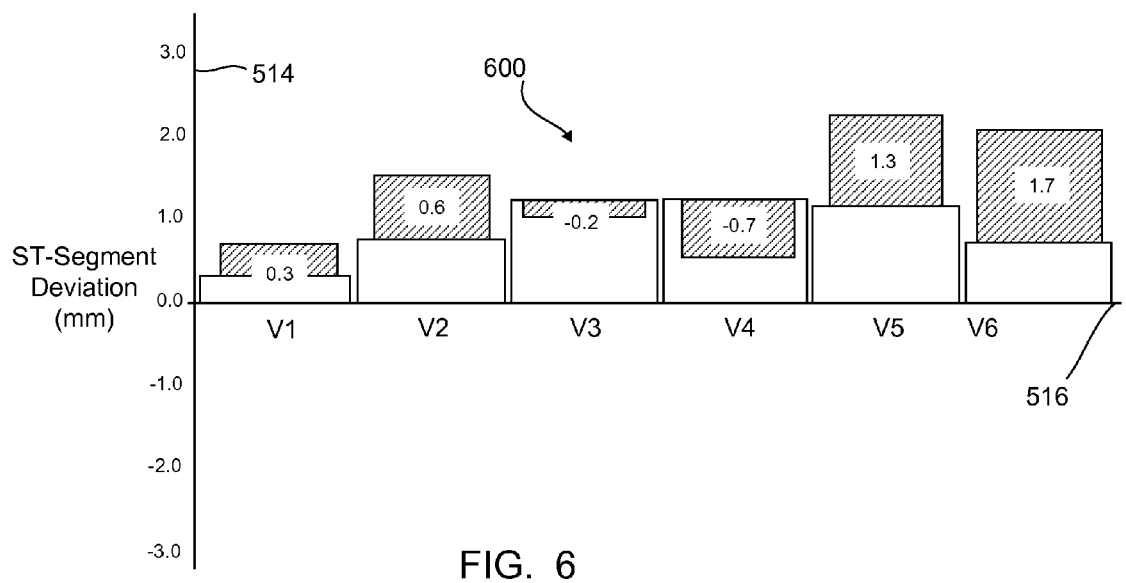
FIG. 6 graphically illustrates a user interface in which a difference between a baseline ST-segment deviation and a current ST-segment deviation changes sign according to one embodiment.

For example, FIG. 6 graphically illustrates a user interface 600 in which a difference between a baseline ST-segment deviation and a current ST-segment deviation changes sign according to one embodiment. In FIG. 6, the current ST-segment deviations for the leads V1, V2, V5, and V6 have increased as compared to their respective baseline ST-segment deviations. However, the current ST-segment deviations for the leads V3 and V4 have decreased as compared to their respective baseline ST-segment deviations.

Accordingly, the second bar graph corresponding to the lead V3 extends from the baseline value back into the first bar graph for the lead V3. In this embodiment, the numerical value "−0.2" is also displayed to indicate that the current ST-segment deviation has decreased by −0.2 mm as compared to the baseline ST-segment deviation. Similarly, the second bar graph corresponding to the lead V4 extends from its baseline ST-segment deviation value back into the first bar graph for the lead V4 and the numerical value "−0.7" is displayed to indicate the difference between the baseline and current values. Because the second bar graphs are narrower than the first bar graphs for the leads V3 and V4, the heights (e.g., baseline values) of the first bar graphs are clearly visible and the differences between the respective baseline and current values are clearly depicted by the highlighted second bar graphs.

Figure 7A:
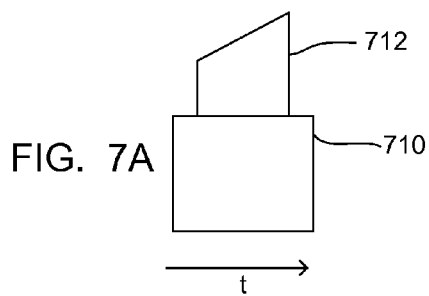
FIGS. 7A, 7B, 7C, and 7D graphically illustrate sloped bar graphs that provide indications of ST-segment deviation trends over time according to certain embodiment.
Figure 7B:
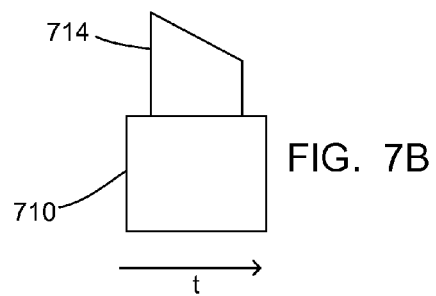

In certain embodiments, at least a portion of the second bar graphs are angled or sloped toward or from their respective current ST-segment deviation values so as to indicate a trend in the ST-segment deviation over time for the respective leads. For example, FIGS. 7A, 7B, 7C, and 7D graphically illustrate sloped bar graphs that provide indications of ST-segment deviation trends over time according to certain embodiment. As discussed above, the height of a first bar graph 710 represents a baseline ST-segment deviation value for a particular lead. In FIG. 7A, the height of a second bar graph 712 represents a current change in the ST-segment deviation value for the particular lead. As shown in FIG. 7A, the top of the second bar graph 712 slopes upward to the right, which corresponds to a direction of increasing time, until it ends at the current ST-segment deviation value. Thus, the upward slope of the second bar graph 712 indicates that the change in ST-segment deviation is currently trending upward. Similarly, in FIG. 7B, the top of a second bar graph 714 slopes downward with time to indicate that the change in ST-segment deviation is currently trending downward.

Figure 7C:
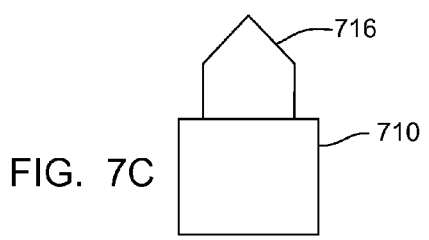
Figure 7D:
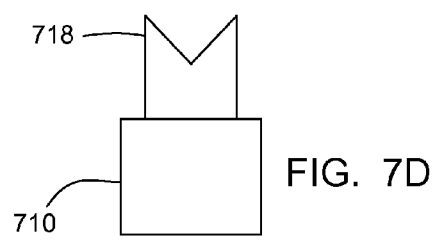

In FIGS. 7C and 7D, the respective slopes are unrelated to a direction of increasing time. Rather, the slopes in these embodiments point in the direction of changing ST-segment deviation. In FIG. 7C, the top of a second bar graph 716 slopes both upward and downward to form an upward pointing peak at the current ST-segment deviation value. The upward pointing peak graphically indicates that the ST-segment deviation is currently trending upward. In FIG. 7D, the top of a second bar graph 718 slopes both downward (from the current ST-segment deviation value) and upward (to the current ST-segment deviation value) to form a downward pointing valley. The downward pointing valley indicates that the ST-segment deviation is currently trending downward. Artisans will recognize from the disclosure herein that other indicia may be provided on or near the second bar graphs to indicate current ST-segment deviation trends. For example, arrows or text such as "up" or "down" may be displayed to indicate the current trends.

Figure 8A:
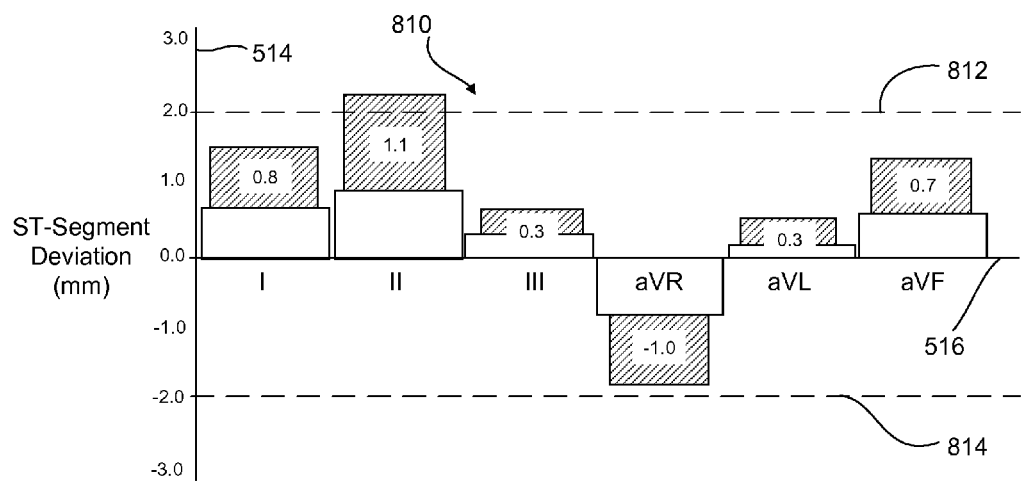
FIGS. 8A and 8B graphically illustrate respective user interfaces displaying threshold lines relative to bar graphs that represent overall ST-segment deviations according to certain embodiments.
Figure 8B:
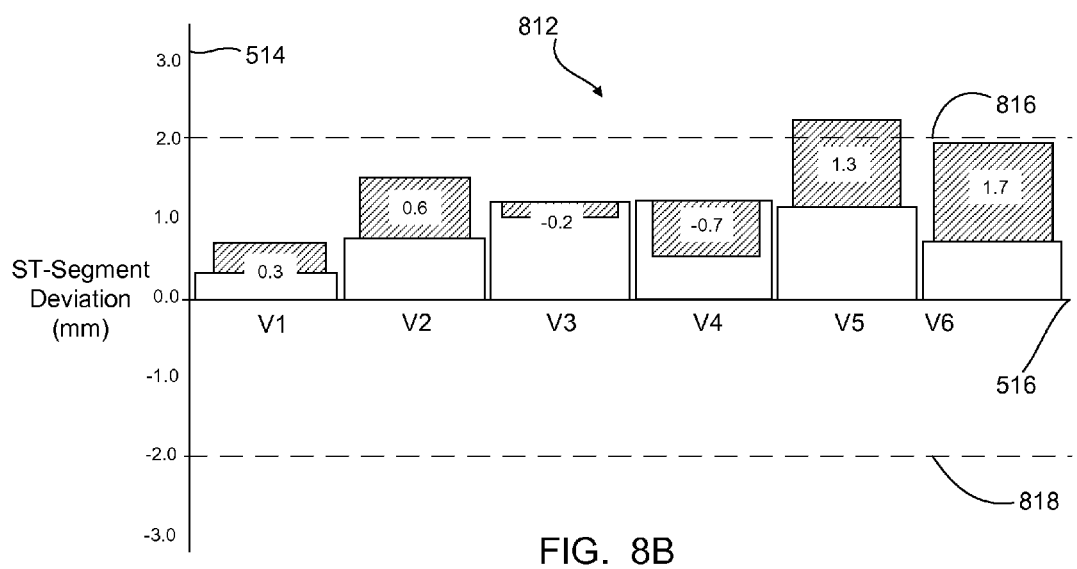

In certain embodiments, one or more threshold lines are displayed relative to the bar graphs to indicate threshold levels at which ST alarms are set. For example, FIGS. 8A and 8B graphically illustrate respective user interfaces 810, 812 displaying threshold lines 812, 814, 816, 818 relative to bar graphs that represent overall ST-segment deviations according to certain embodiments. In this example, upper threshold lines 812, 816 are set at 2.0 mm and lower threshold lines are set at −2.0 mm. As shown in FIG. 8A, the current ST-segment deviation value of the lead II has surpassed the upper threshold line 812. As shown in FIG. 8B, the current ST-segment deviation value of the lead V5 has surpassed the upper threshold line 816.

In certain embodiments, the highlighting of the second bar graph changes when it reaches one of the threshold lines 812, 814, 816, 818. For example, the second bar graph for the lead II in FIG. 8A may change colors (e.g., from green to blue) when the current ST-segment deviation first reaches 2.0 mm. Other responses to reaching an ST alarm limit include, for example, causing the second bar graph to flash, sounding an audible alarm, providing an alarm signal to a remote device or system, or combinations of the foregoing.

In certain embodiments, a user may independently set the respective threshold lines 812, 814, 816, 818 at any value. For example, the user may set the limb (FIG. 8A) upper threshold line 812 to 2.5 mm and lower threshold line 814 to −3.0 mm, and the precordial (FIG. 8B) upper threshold line 816 to 1.5 mm and the lower threshold line 818 to −1.0 mm. In other embodiments, the user may selectively set threshold lines for each lead independently. In FIG. 8A, for example, the user may set a first upper threshold line (not shown) for the lead II to 2.5 mm and a second upper threshold line (not shown) for limb III to 1.5 mm. As another example, in some embodiments, a user may set a single threshold value, such as 1.0 mm, that is automatically applied to the relative changes in each lead. In such embodiments, the user interface displays a different threshold line for each lead that is 1.0 mm (in this example) above or below the baseline ST-segment deviation value for that lead. If, for example, the baseline ST-segment value for a particular lead is 1.1 mm, then the user interface would display a threshold line of 2.1 mm for that lead. Similarly, if the baseline ST-segment value for a particular lead is −0.5 mm, then the user interface would display a threshold line of −1.5 mm for that lead. An artisan will recognize from the disclosure herein that the threshold values disclosed are provided by way of example only, and not by way of limitation.

Because ST-segment measurements are generally represented as relative changes with respect to baseline values, and because ST alarms are generally set based on such relative changes, some embodiments display threshold lines with respect to only relative changes in ST-segment deviation. For example, FIGS. 9A and 9B graphically illustrate respective user interfaces 910, 912 displaying threshold lines 912, 914, 916, 918 relative to bar graphs that represent only relative ST-segment deviations according to certain embodiments. In this example, upper threshold lines 912, 916 are set at 1.0 mm and lower threshold lines 914, 918 are set at −1.0 mm.

Figure 9A:
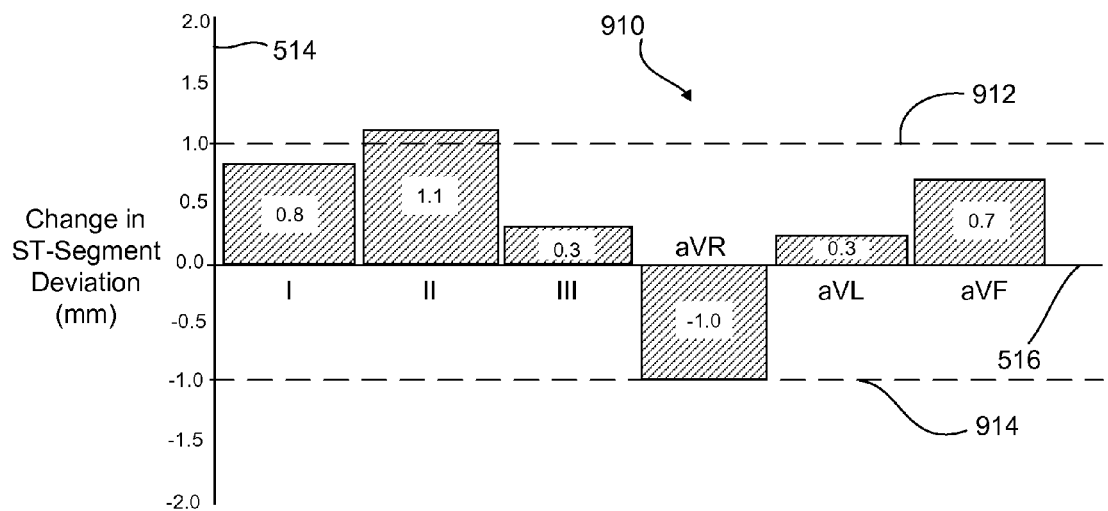
FIGS. 9A and 9B graphically illustrate respective user interfaces displaying threshold lines relative to bar graphs that represent only relative ST-segment deviations according to certain embodiments.
Figure 9B:
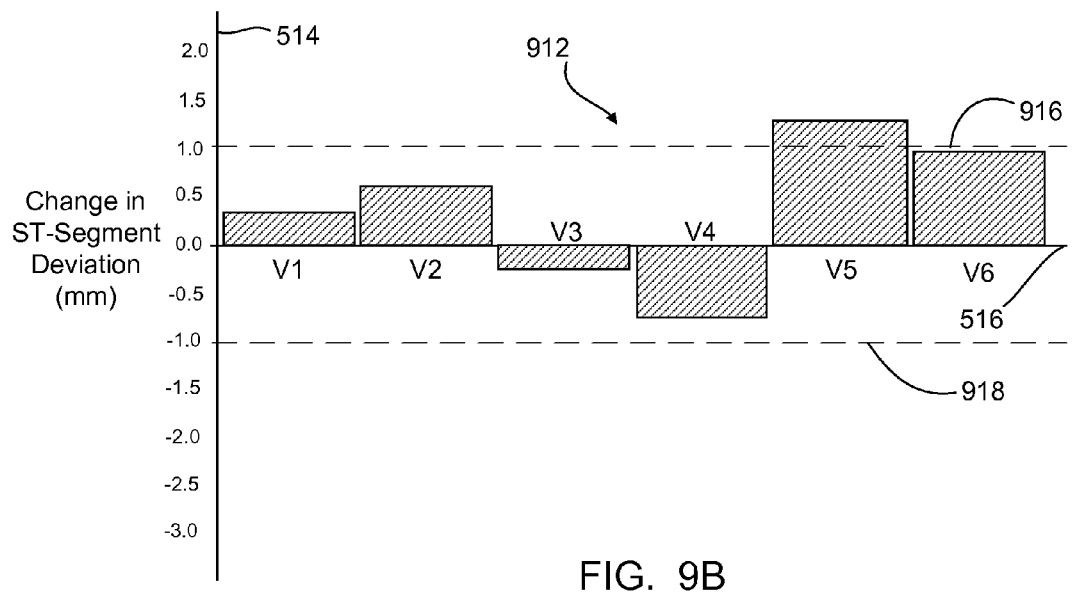

As compared to the embodiments discussed above, the first bar graphs representing the baseline ST-segment deviations are not shown in the embodiments of FIGS. 9A and 9B. Rather, only bar graphs are shown that represent differences between the baseline and current ST-segment deviation values. Accordingly, the 0.0 mm value along the first linear axis 514 represents zero change from each respective lead's baseline ST-segment deviation value. Thus, each displayed bar graph begins at 0.0 mm and ends at the difference between its respective baseline and current ST-segment deviation values.

Figure 10:
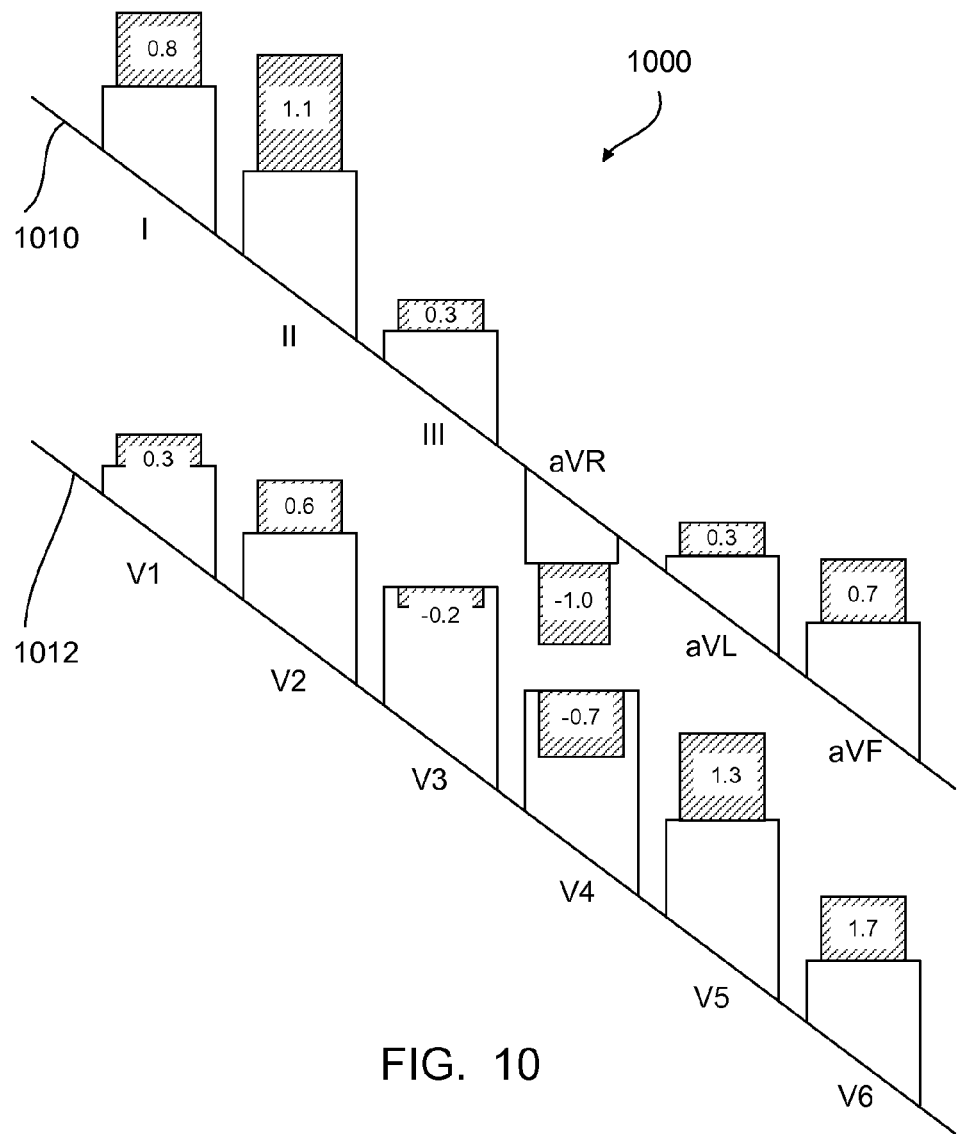
FIG. 10 graphically illustrates a user interface displaying a first axis along which bar graphs for limb leads are displayed and a second axis along with bar graphs for precordial leads are displayed according to one embodiment.

While certain embodiments discussed above display graphs for certain leads in a first window (or first portion of a window) and graphs for other leads in a second window (or second portion of a window), the disclosure herein is not so limited. For example, bar graphs for both limb leads and precordial leads may be displayed in the same window or along the same set of axes 514, 516. Further, in certain embodiments, both axes 514, 516 need not be displayed. For example, FIG. 10 graphically illustrates a user interface 1000 displaying a first axis 1010 along which bar graphs for limb leads are displayed and a second axis 1012 along with bar graphs for precordial leads are displayed according to one embodiment. In this example, the axes 1010, 1012 are parallel to each other, but slanted at an angle so as to fit all of the bar graphs within a predetermined space on a single display device.

In certain embodiments, rather than displaying bar graphs, other graphic indicia are displayed to represent ST-segment deviation. For example, FIG. 11 graphically illustrates a user interface 1100 for displaying a plot of ST-segment deviation values according to one embodiment. In this example, baseline ST-segment deviations are represented by darkened squares 1110 that are plotted relative to their respective values (e.g., between 3.0 mm and −3.0 mm) shown along a first axis 514 and their respective leads (e.g., limb leads I, II, III, aVR, aVL, and aVF) shown along a second axis 516. Similarly, current ST-segment deviations are represented in this example by (undarkened) squares 1112 that are plotted relative to their respective values shown along the first axis 514 and their respective leads shown along the second axis 516. Of course, any graphic symbol may be used to represent the ST-segment deviation values such as squares, circles, diamonds, stars, asterisks, or any other shapes. Further, as discussed above, highlighting such as different shadings or colors may be used to distinguish between the baseline and current ST-segment deviation values.

Figure 12:
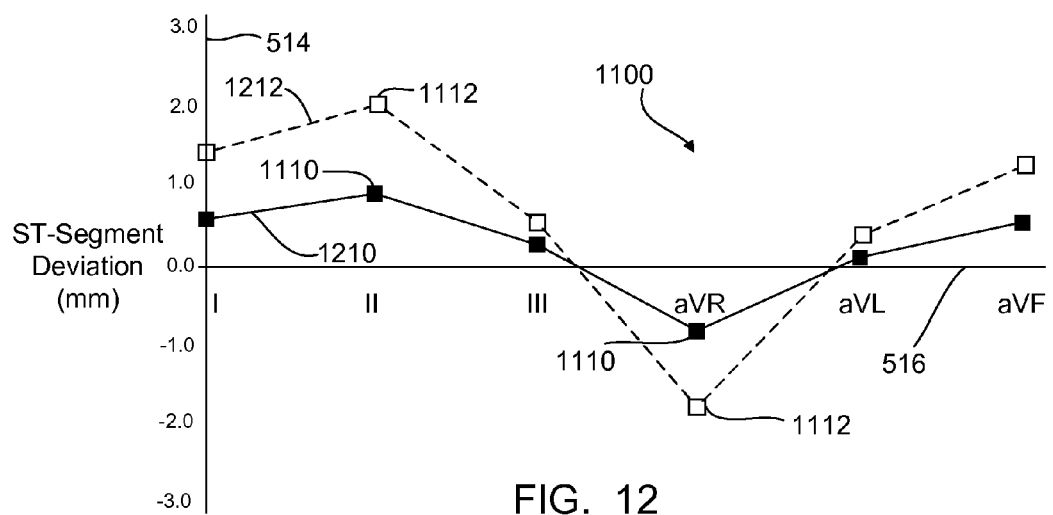

Further, as shown in FIG. 12, the graphic indicia may be connected by line segments 1210, 1212. In the example of FIG. 12, the darkened squares 1110 representing baseline ST-segment deviations are connected by solid line segments 1210 and the squares 1112 representing current ST-segment deviations are connected by dashed line segments 1212. In addition, or in other embodiments, the line segments 1210, 1212 may be different colors to distinguish between baseline and current ST-segment deviations. Connecting the data points with the respective line segments 1210, 1212 helps the user to quickly interpret the data. For example, over time, the user can visually observe the area between the two curves created by the two sets of line segments 1210, 1212. An increasing area between the two curves indicates, for example, a worsening ischemia.

Figure 11:
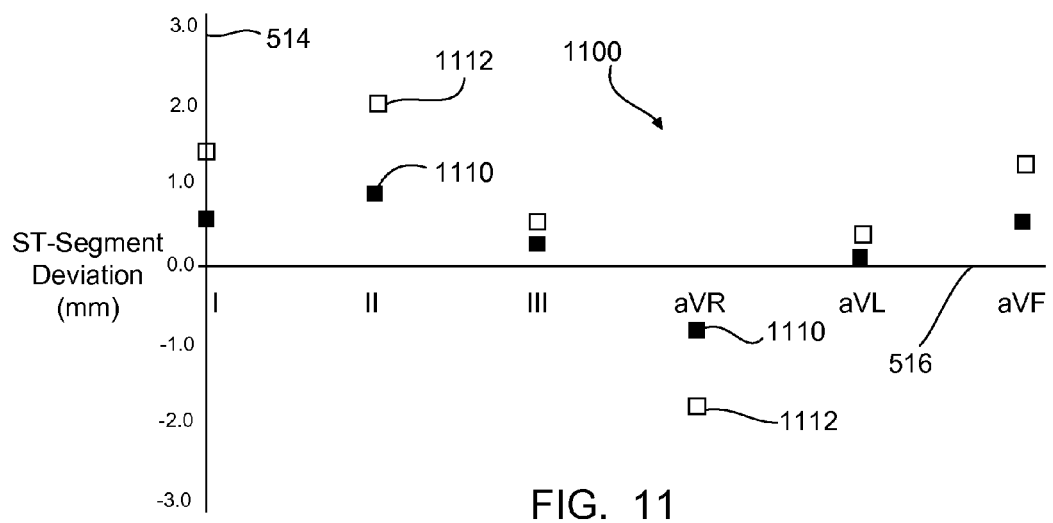
FIGS. 11 and 12 graphically illustrate respective user interfaces for displaying plots of ST-segment deviation values according to certain embodiments.
Figure 13A:
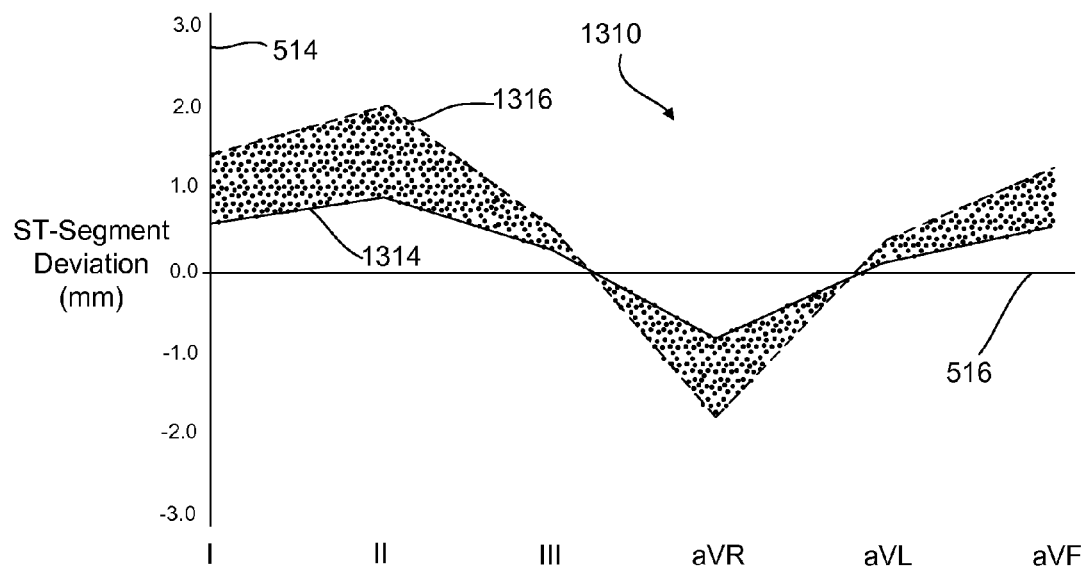
FIGS. 13A and 13B graphically illustrate respective user interfaces displaying highlighting between a first line graph representing baseline ST-segment deviations and a second line graph representing current ST-segment deviations according to certain embodiments.
Figure 13B:
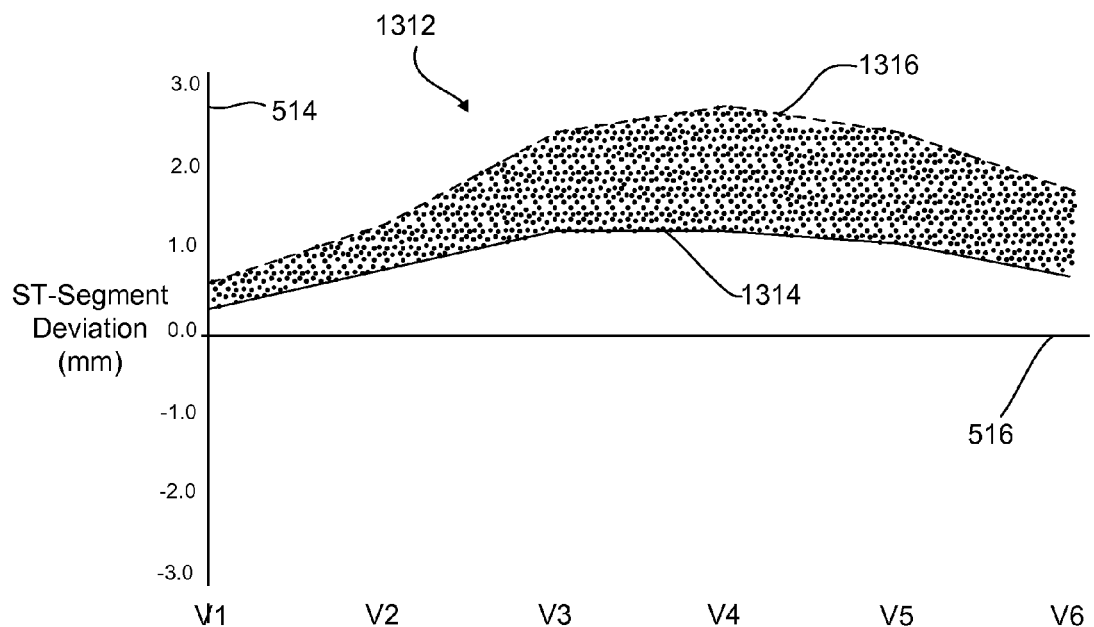

In certain embodiments, the area between the two curves may be highlighted. For example, FIGS. 13A and 13B graphically illustrate respective user interfaces 1310, 1312 displaying highlighting between a first line graph 1314 representing baseline ST-segment deviations and a second line graph 1316 representing current ST-segment deviations according to certain embodiments. FIG. 13A represents limb leads (e.g., I, II, III, aVR, aVL, and aVF) and FIG. 13B represents precordial leads (e.g., V1, V2, V3, V4, V5, and V6). In this example, the squares 1110, 1112 shown in FIGS. 11 and 12 are not displayed. Rather, the graphic indicia are simply the line segments that extend between respective baseline and current ST-segment deviation values.

For illustrative purposes, the highlighting in FIGS. 13A and 13B is represented by shading with small dots. In other embodiments, as discussed above, the highlighting may include other types of shading, hatching, coloring, or combinations of the foregoing. Further, the highlighting in certain embodiments may change when an ST alarm condition is met. The alarm condition may be met, as discussed above, when a current ST-segment deviation value (or difference between a current value and a baseline value) reaches a predetermined threshold.

Figure 14:
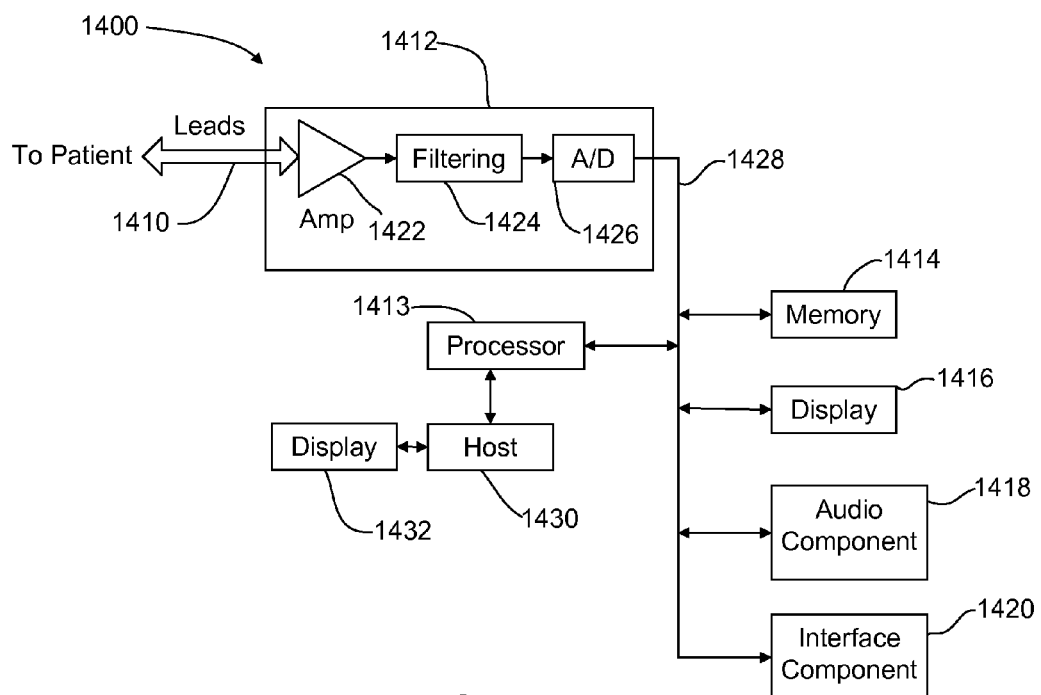
FIG. 14 is a simplified block diagram of a system 1400 for monitoring ST-segment deviation according to one embodiment.

FIG. 14 is a simplified block diagram of a system 1400 for monitoring ST-segment deviation according to one embodiment. The system 1400 includes a plurality of leads 1410 electrically connected to a receiver component 1412 that is in communication with a processor 1413, a memory device 1414, a display device 1416, an audio component 1418, and an interface component 1420. The leads 1410 include wires and electrodes configured to attach to a patient (not shown) to detect ECG signals. The receiver 1412 may include, for example, an amplification component 1422 to amplify the ECG signals detected by the leads 1410, a filtering component 1424 to eliminate undesirable noise from the ECG signals, and an analog-to-digital (ND) converter 1426 to provide converted ECG signals through a system bus 1428 to the processor 1413.

The processor 1413 may include a special purpose processor configured to perform the processes described herein. In another embodiment, the processor 1413 is a general purpose processor configured to execute computer executable instructions (e.g., stored in computer-readable medium such as the memory device 1414) to perform the processes described herein. In addition, or in other embodiments, the processor 1413 may be connected to a host computer 1430 having a display device 1432. The host computer 1430 may include computer executable instructions for performing the processes described herein. The host computer 1430 may be used in certain embodiments, for example, to provide remote patient monitoring.

In one embodiment, the system 1400 allows a clinician to select data corresponding to one or more of the leads for display. The system 1400 then automatically monitors and displays the selected data on at least one of the display devices 1416, 1432. In certain embodiments, the audio component 1418 provides an audible alarm and/or verbal annunciation of ST-segment deviations that exceed a defined threshold. The interface component 1420 may include, for example, an integrated keypad, touch screen, or other user controls. The interface component 1420 may also include, for example, interfaces for an external keyboard, a mouse, a printer, an external storage device, and/or a network adapter.

It will be understood by those having skill in the art that many changes may be made to the details of the above-described embodiments without departing from the underlying principles of the invention. The scope of the present invention should, therefore, be determined only by the following claims.

The invention claimed is:

1. A method for monitoring a patient and graphically representing ST-segment deviations, the method comprising:
  acquiring electrocardiogram (ECG) signals from a plurality of leads, each ECG signal including a sequence of ST-segments between a QRS complex and a T wave;
  determining a baseline ST-segment deviation from an isoelectric value for each of the plurality of leads;

determining a current ST-segment deviation from the isoelectric value for each of the plurality of leads;
displaying a graph comprising:
a first linear axis representing ST-segment deviation values; and
a second linear axis representing the plurality of leads, wherein each of the plurality of leads is associated with a respective location along the second linear axis;
displaying a first set of bar graphs representing the baseline ST-segment deviations, wherein each first bar graph is displayed with respect to one of the locations corresponding to a respective lead and is aligned relative to the first linear axis based on the baseline ST-segment deviation for the respective lead; and
displaying a second set of bar graphs representing the current ST-segment deviations, wherein each second bar graph is displayed with respect to one of the locations corresponding to a respective lead and is aligned relative to the first linear axis based on the current ST-segment deviation for the respective lead;
wherein each second bar graph has a width in the direction of the second linear axis that is narrower than a width in the direction of the second linear axis of the corresponding first bar graph for a respective lead;
wherein each second bar graph has an origin with respect to the first axis at the baseline ST-segment deviation for a respective lead and extends along the first axis in a positive or negative direction depending on whether the current ST-segment deviation is respectively greater or less than the baseline ST-segment deviation; and
wherein, if the current ST-segment deviation is positive and is less than the baseline ST-segment deviation for a particular lead, the second bar graph for the particular lead extends in the negative direction into the corresponding first bar graph.

2. The method of claim 1, wherein displaying each first bar graph comprises:
displaying the first bar graph between a first value relative to the first linear axis and a second value relative to the first linear axis, wherein the first value corresponds to the isoelectric value, and wherein the second value corresponds to the baseline ST-segment deviation for the respective lead.

3. The method of claim 2, wherein displaying each second bar graph comprises:
displaying the second bar graph between the second value relative to the first linear axis and a third value relative to the first linear axis, wherein the third value corresponds to the current ST-segment deviation for the respective lead.

4. The method of claim 1, further comprising:
highlighting, at each of the locations along the second linear axis, at least one of the first bar graph and the second bar graph to visually distinguish the first bar graphs from the second bar graphs.

5. The method of claim 4, wherein the highlighting comprises one or more graphical elements selected from the group comprising shading and coloring.

6. The method of claim 5, further comprising:
displaying one or more threshold lines substantially parallel to the second linear axis, each threshold line representing a threshold ST-segment deviation value;
determining that at least one of the second bar graphs intersects one of the threshold lines; and
in response to the determination, changing the highlighting of the at least one second bar graphs that intersects one of the threshold lines.

7. The method of claim 1, wherein displaying the graph comprises:
displaying a first portion of the graph in a first window, the first portion corresponding to a first subset of leads; and
displaying a second portion of the graph in a second window, the second portion corresponding to a second subset of leads.

8. The method of claim 7, wherein the first subset of leads includes limb leads and the second subset of leads includes precordial leads.

9. A patient monitoring system for graphically representing ST-segment deviation, the system comprising:
a receiver to acquire electrocardiogram (ECG) signals through a plurality of leads, the ECG signals including an ST-segment between a QRS complex and a T wave;
a processor to process the ECG signals to determine, for each of the plurality of leads, baseline ST-segment deviations from an isoelectric value and current ST-segment deviations from the isoelectric value;
a display device for displaying a user interface; and
a display module for displaying a graph in the user interface, the graph comprising:
a first linear axis representing ST-segment deviation values; and
a second linear axis representing the plurality of leads, wherein each of the plurality of leads is associated with a respective location along the second linear axis;
wherein the display module displays a first set of bar graphs representing the baseline ST-segment deviations, each first bar graph being displayed with respect to one of the locations corresponding to a respective lead and being aligned relative to the first linear axis based on the baseline ST-segment deviation for the respective lead; and
wherein the display module displays a second set of graphic indicia representing the current ST-segment deviations, each second bar graph being displayed with respect to one of the locations corresponding to a respective lead and being aligned relative to the first linear axis based on the current ST-segment deviation for the respective lead;
wherein each second bar graph has a width in the direction of the second linear axis that is narrower than a width in the direction of the second linear axis of the corresponding first bar graph for a respective lead;
wherein each second bar graph has an origin with respect to the first axis at the baseline ST-segment deviation for a respective lead and extends along the first axis in a positive or negative direction depending on whether the current ST-segment deviation is respectively greater or less than the baseline ST-segment deviation; and
wherein, if the current ST-segment deviation is positive and is less than the baseline ST-segment deviation for a particular lead, the second bar graph for the particular lead extends in the negative direction into the corresponding first bar graph.

10. The system of claim 9 wherein the display module is further configured to:
display the first bar graph between a first value relative to the first linear axis and a second value relative to the first linear axis, wherein the first value corresponds to the isoelectric value, and wherein the second value corresponds to the baseline ST-segment deviation for the respective lead; and display the second bar graph between the second value relative to the first linear axis and a third value relative to the first linear axis, wherein the third value corresponds to the current ST-segment deviation for the respective lead.

11. The system of claim 9 wherein the display module is further configured to:

highlight, at each of the locations along the second linear axis, at least one of the first bar graph and the second bar graph to visually distinguish the first bar graphs from the second bar graphs.

12. The system of claim 11, wherein the highlighting comprises one or more graphical elements selected from the group comprising shading and coloring.

13. The system of claim 12, wherein the display module is further configured to:

display one or more threshold lines substantially parallel to the second linear axis, each threshold line representing a threshold ST-segment deviation value;

determine that at least one of the second bar graphs intersects one of the threshold lines; and in response to the determination, change the highlighting of the at least one second bar graphs that intersects one of the threshold lines.

14. The system of claim 9, wherein the display module is further configured to:

display a first portion of the graph in a first window, the first portion corresponding to a first subset of leads; and display a second portion of the graph in a second window, the second portion corresponding to a second subset of leads.

15. The system of claim 14, wherein the first subset of leads includes limb leads and the second subset of leads includes precordial leads.

16. A patient monitoring system for graphically representing ST-segment deviation, the system comprising:

means for acquiring electrocardiogram (ECG) signals through a plurality of leads, the ECG signals including an ST-segment between a QRS complex and a T wave;

means for processing the ECG signals to determine, for each of the plurality of leads, baseline ST-segment deviations from an isoelectric value and current ST-segment deviations from the isoelectric value;

means for displaying a user interface; and means for displaying a graph in the user interface, the graph comprising:

a first linear axis representing ST-segment deviation values; and a second linear axis representing the plurality of leads, wherein each of the plurality of leads is associated with a respective location along the second linear axis;

wherein the means for displaying displays a first set of bar graphs representing the baseline ST-segment deviations, each first bar graph being displayed with respect to one of the locations corresponding to a respective lead and being aligned relative to the first linear axis based on the baseline ST-segment deviation for the respective lead; and wherein the means for displaying displays a second set of bar graphs representing the current ST-segment deviations, each second bar graph being displayed with respect to one of the locations corresponding to a respective lead and being aligned relative to the first linear axis based on the current ST-segment deviation for the respective lead;

wherein each second bar graph has a width in the direction of the second linear axis that is narrower than a width in the direction of the second linear axis of the corresponding first bar graph for a respective lead;

wherein each second bar graph has an origin with respect to the first axis at the baseline ST-segment deviation for a respective lead and extends along the first axis in a positive or negative direction depending on whether the current ST-segment deviation is respectively greater or less than the baseline ST-segment deviation; and wherein, if the current ST-segment deviation is positive and is less than the baseline ST-segment deviation for a particular lead, the second bar graph for the particular lead extends in the negative direction into the corresponding first bar graph.

\* \* \* \* \*